US010130669B2

(12) United States Patent
Gilbert

(10) Patent No.: US 10,130,669 B2
(45) Date of Patent: Nov. 20, 2018

(54) METHOD AND SYSTEM FOR TREATING WOUNDS

(71) Applicant: Ronald K. Gilbert, Bradenton, FL (US)

(72) Inventor: Ronald K. Gilbert, Bradenton, FL (US)

(*) Notice: Subject to any disclaimer, the term of this patent is extended or adjusted under 35 U.S.C. 154(b) by 702 days.

(21) Appl. No.: 14/583,985

(22) Filed: Dec. 29, 2014

(65) Prior Publication Data

US 2016/0184603 A1 Jun. 30, 2016

(51) Int. Cl.
| | |
|---|---|
| *A61N 5/06* | (2006.01) |
| *A61K 33/00* | (2006.01) |
| *A61K 36/61* | (2006.01) |
| *A61K 36/53* | (2006.01) |
| *A61K 31/194* | (2006.01) |
| *A61K 38/08* | (2006.01) |
| *A61K 31/351* | (2006.01) |
| *A61M 37/00* | (2006.01) |
| *A61K 31/79* | (2006.01) |
| *A61K 38/14* | (2006.01) |
| *A61K 31/07* | (2006.01) |

(Continued)

(52) U.S. Cl.
CPC ........ *A61K 36/53* (2013.01); *A61F 13/00004* (2013.01); *A61K 31/07* (2013.01); *A61K 31/122* (2013.01); *A61K 31/194* (2013.01); *A61K 31/351* (2013.01); *A61K 31/355* (2013.01); *A61K 31/375* (2013.01); *A61K 31/593* (2013.01); *A61K 33/00* (2013.01); *A61K 33/02* (2013.01); *A61K 33/18* (2013.01); *A61K 33/30* (2013.01); *A61K 36/61* (2013.01); *A61K 38/14* (2013.01); *A61N 5/0616* (2013.01); *A61F 2013/00285* (2013.01); *A61M 2037/0007* (2013.01); *A61M 2202/0468* (2013.01); *A61N 2005/067* (2013.01); *A61N 2005/0659* (2013.01); *A61N 2005/0662* (2013.01); *A61N 2005/0663* (2013.01)

(58) Field of Classification Search
CPC .... A61K 36/53; A61K 31/194; A61K 31/351; A61K 31/79; A61K 33/00; A61K 36/61; A61K 38/14; A61F 13/00004; A61F 2013/00285; A61N 5/0616; A61N 2005/0659; A61N 2005/0662; A61N 2005/0663; A61N 2005/067; A61M 2037/0007; A61M 2202/0468
USPC ............................................ 606/89; 424/450
See application file for complete search history.

(56) References Cited

U.S. PATENT DOCUMENTS

| | | | |
|---|---|---|---|
| 6,165,205 A | 12/2000 | Neuberger | |
| 2008/0020025 A1* | 1/2008 | Giles | A61K 33/00 424/446 |

(Continued)

*Primary Examiner* — Gary Jackson
*Assistant Examiner* — Zahed Kabir
(74) *Attorney, Agent, or Firm* — Ariel Bentolila; Bay Area IP

(57) ABSTRACT

A method and a system comprise receiving an amount of a first disinfecting solution on and around a wound. An amount of a second disinfecting solution is received on and around the wound. An amount of a third disinfecting solution is received on and around the wound. An amount of a fourth disinfecting solution is received around the wound. Cold laser emissions are received on and around the wound. The cold laser emissions comprise at least multiple wavelengths. A sterile gauze bandage and wrap cover the wound.

21 Claims, 3 Drawing Sheets

(51) Int. Cl.
    *A61K 31/122* (2006.01)
    *A61K 31/355* (2006.01)
    *A61K 31/375* (2006.01)
    *A61K 31/593* (2006.01)
    *A61K 33/02* (2006.01)
    *A61K 33/18* (2006.01)
    *A61K 33/30* (2006.01)
    *A61N 5/067* (2006.01)
    *A61F 13/00* (2006.01)

(56) References Cited

U.S. PATENT DOCUMENTS

| | | | |
|---|---|---|---|
| 2008/0215020 A1* | 9/2008 | Reeves | A61F 13/00068 |
| | | | 604/305 |
| 2009/0148502 A1* | 6/2009 | Pronovost | A61L 15/18 |
| | | | 514/1.1 |
| 2010/0062048 A1* | 3/2010 | Hsia | A61K 9/0014 |
| | | | 424/450 |
| 2013/0203663 A1 | 8/2013 | Mager et al. | |
| 2013/0230609 A1* | 9/2013 | Modak | A01N 65/44 |
| | | | 424/739 |
| 2016/0022655 A1* | 1/2016 | Veenstra | A61K 36/61 |
| | | | 424/682 |

\* cited by examiner

METHOD AND SYSTEM FOR TREATING WOUNDS

CROSS-REFERENCE TO RELATED APPLICATIONS

Not applicable.

RELATED CO-PENDING U.S. PATENT APPLICATIONS

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the invention generally relate to wound healing. More particularly, the invention relates to a method and apparatus to treat acute and chronic wounds.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. Proper wound care may aid in the speed of healing, the prevention of infection, reduction of scarring, etc. However, it is believed that some acute and chronic wounds may be unresponsive to conventional treatment regimens. For example, over 30% of hospital wound center patients may not have healed wounds even after many weeks of treatment. Conventional healing treatments may include, without limitation, topical, oral, and IV antibiotics for treatment of infected wounds, hyperbaric oxygen treatment, surgical and enzymatic wound debridement for wound closure assistance, the use of vacuum assistive closure, etc. Some existing techniques may be extremely costly. One can observe that the failure to properly heal a wound may often result in infection, and amputation as a last resort. These may severely change the lifestyle and subsequent health of the patient, death, uncertainty, etc. Amputation may be particularly likely in patients with diabetes, as diabetes in many cases may cause complications that may increase susceptibility to infection and may hinder wound healing. Due to the constant danger of complications with wound healing, acute and chronic wounds in diabetes patients are believed to be the cause of nearly 60% of non-traumatic lower-limb amputations.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, an aspect of the prior art generally useful to be aware of is that there are currently some approaches available for aiding or accelerating wound healing which may be used with conventional techniques or instead of conventional techniques. One such approach teaches a method and apparatus for localized low energy photon therapy (LEPT). Another approach teaches an apparatus and method for a pulsed electromagnetic energy treatment apparatus and method. This method typically uses only a pulsed electromagnetic energy treatment directly on or adjacent to a wound and generally does not specifically address bacterial infection, circulatory changes to the wound area, nutritional or biomechanical aspects for wound healing, etc. Yet another current wound healing approach may use a transdermal therapeutic patch to introduce a therapeutic substance into a wound and then expose the patch to an electromagnetic pulse in a specified UV light range of $\lambda=365$ nm. Yet another approach shows a method and apparatus for therapeutic laser treatment of wounds. It is believed that the applied laser energy in this method often causes damage or inflammation to the tissue of the patient to promote reactive healing. Other approaches may use various different substances to aid in healing such as, but not limited to, an extracellular polymeric substance solvating system, angiogenic crystallin proteins and/or endothelial cell migration, specifically Alpha (x) A-crystallin and βB2 crystallin, regenerative stem cells in vivo and in situ, TNF antagonist, TACE inhibitors, a neutrophil antagonist, a combination of a TNF antagonist and/or a TACE inhibitor and a neutrophil antagonist, specifically alefacept, efalizumab, etanercept, adalimumab, onercept, dapsone, colchicine, or analogs of such and prodrugs, sulfapyridine, sulfasalazine, mesalamine, or any derivatives. Furthermore, due to the benefits good nutrition may have on the body, one may expect that the consumption of various different nutrients may aid in wound healing. It is believed that nutrient intake may affect type-2 diabetes. It is also believed that Vitamin D3 may be important in combatting bacterial infections. It is further believed that coenzyme $Q_{10}$ may have a role in management of chronic heart failure. It is also believed that intake of n-3 Fatty acids may benefit cardiovascular disease and type-2 diabetes outcomes. It is further believed that zinc supplementation may lower the incidence of infection. One current approach employs tube feeding formulations and methods for using same to promote wound healing. However, tube feeding may be dangerous, inconvenient, uncomfortable, or otherwise undesirable for some patients.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accom

Figure 1:
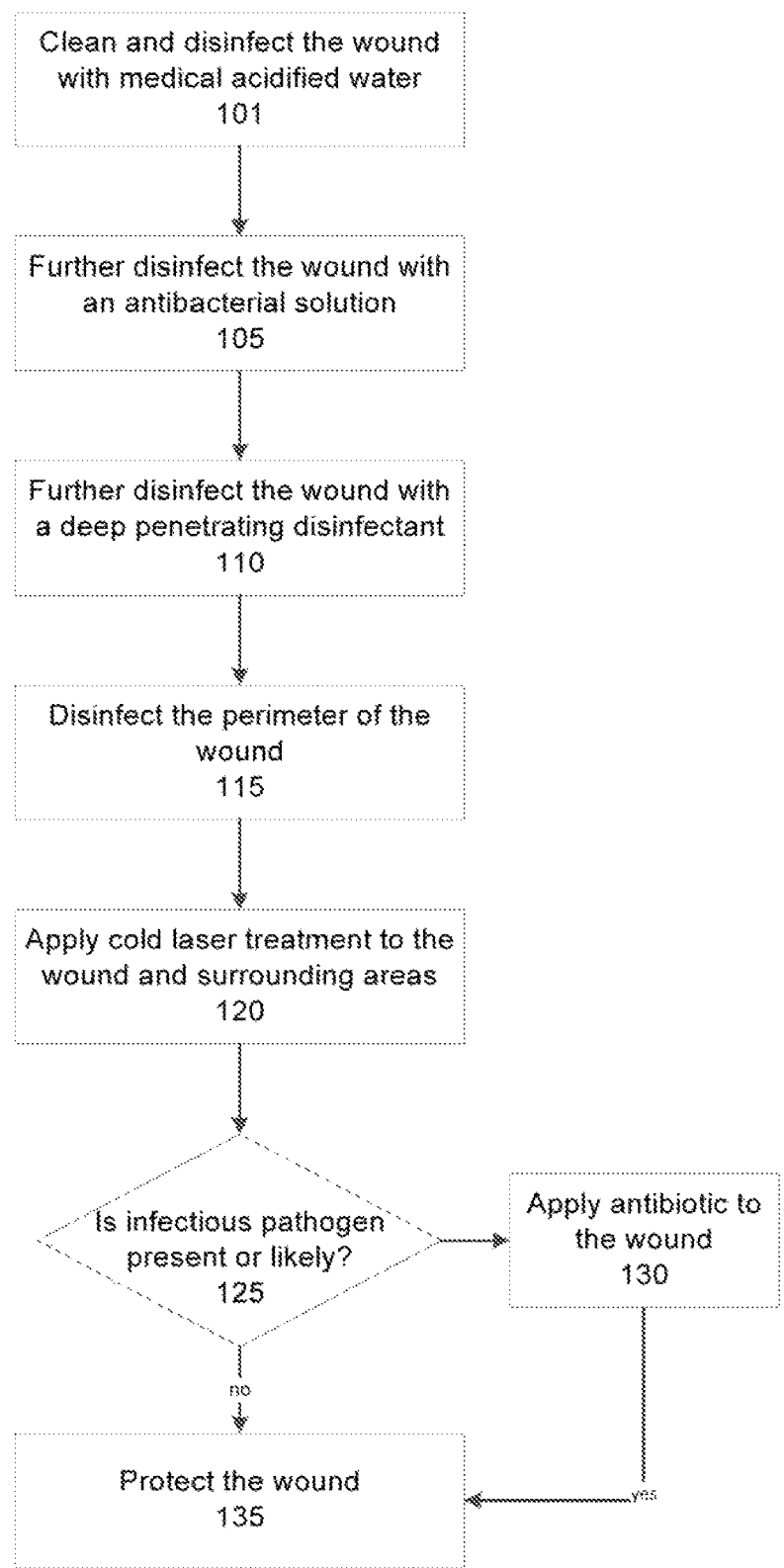
- FIG. 1 is a flowchart illustrating an exemplary process for wound treatment in a medical setting, in accordance with an embodiment of the present invention.

Unless otherwise indicated illustrations in the figures are not necessarily drawn to scale.

DETAILED DESCRIPTION OF SOME EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

Headings provided herein are for convenience and are not to be taken as limiting the disclosure in any way.

The enumerated listing of items does not imply that any or all of the items are mutually exclusive, unless expressly specified otherwise.

It is understood that the use of specific component, device and/or parameter names are for example only and not meant to imply any limitations on the invention. The invention may thus be implemented with different nomenclature/terminology utilized to describe the mechanisms/units/structures/components/devices/parameters herein, without limitation. Each term utilized herein is to be given its broadest interpretation given the context in which that term is utilized.

Terminology. The following paragraphs provide definitions and/or context for terms found in this disclosure (including the appended claims):

"Comprising." This term is open-ended. As used in the appended claims, this term does not foreclose additional structure or steps. Consider a claim that recites: "A memory controller comprising a system cache . . . ." Such a claim does not foreclose the memory controller from including additional components (e.g., a memory channel unit, a switch).

"Configured To." Various units, circuits, or other components may be described or claimed as "configured to" perform a task or tasks. In such contexts, "configured to" or "operable for" is used to connote structure by indicating that the mechanisms/units/circuits/components include structure (e.g., circuitry and/or mechanisms) that performs the task or tasks during operation. As such, the mechanisms/unit/circuit/component can be said to be configured to (or be operable) for perform(ing) the task even when the specified mechanisms/unit/circuit/component is not currently operational (e.g., is not on). The mechanisms/units/circuits/components used with the "configured to" or "operable for" language include hardware—for example, mechanisms, structures, electronics, circuits, memory storing program instructions executable to implement the operation, etc. Reciting that a mechanism/unit/circuit/component is "configured to" or "operable for" perform(ing) one or more tasks is expressly intended not to invoke 35 U.S.C. .sctn.112, sixth paragraph, for that mechanism/unit/circuit/component. "Configured to" may also include adapting a manufacturing process to fabricate devices or components that are adapted to implement or perform one or more tasks.

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

The terms "a", "an" and "the" mean "one or more", unless expressly specified otherwise.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

It is to be understood that any exact measurements/ dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

An embodiment of the present invention may provide a holistic and allopathic approach to acute and chronic wound treatment using natural methods. This approach may minimize side effects of oral and topical antibiotics. Some embodiments may comprise a stepwise technique for sterilization of a wound that may use a combination of wound sterilizing, sanitizing, and healing agents such as, but not limited to, acidified water, Sol-u-guard™, tea tree oil, etc. which may help to prevent or eradicate infection. Some embodiments may also use a cold laser to assist with wound tissue regeneration and healing. Some embodiments may also use micro and macronutrients such as, but not limited to, vitamins and whole foods and nutritional counseling, which may assist in enhancing immune function and promoting the body's natural healing ability. Some embodiments may also use manipulation techniques to adjust body mechanics including, but not limited to, chiropractic, osteopathic, or orthopedic methods to improve function and assist in wound healing. Wound treatment processes according to some embodiments of the present invention may be used as the sole method for wound treatment or may be used congruently with conventional methods of wound treatment. For example, without limitation, these processes may be used as a supplement for wound care, in both new and chronic wounds or may be used as an initial process for wound care to potentially increase healing prior to the use of antibiotics, surgical debridement, and other conventional wound treatment techniques. Some embodiments may be effective in healing refractory wounds, which are wounds that do not heal with conventional means. Furthermore, approaches according to some embodiments may be more cost effective for the patient and may provide quicker results for the care giver than conventional methods.

FIG. 1 is a flowchart illustrating an exemplary process for wound treatment in a medical setting, in accordance with an embodiment of the present invention. In the present embodiment, the treatment process comprises multiple steps for wound treatment in a doctor's office, hospital, clinic, etc. This process may then be followed by a process for wound care at home as illustrated by way of example in FIG. 2. However, some alternate embodiments may be implemented without the in home treatment process; for example, without limitation, if the patient is admitted to the hospital or is recovering from surgery. In the present embodiment, the in office process begins at step 101 in which medical acidified water is applied on and around the wound with an applicator such as, but not limited to, a sprayer, an eyedropper, a sterile cotton swab, etc. Typically, enough acidified water is applied to saturate the wound entirely to produce a sterile field. It is contemplated that the medical acidified water may have a preferred range of a pH balance between 2.54 and 5.72. A larger range of a pH level between 2.3 and 6.5 may be used in some embodiments even if not optimal. Those skilled in the art will readily recognize, in light of and in accordance with the teachings of the present invention, that various different methods may be used to make the acidified water including, but not limited to, using a Biontech BTM3000 machine to convert spring water or water purified by reverse osmosis into acidified water in a 60 minute cycle. The caregiver should always wear gloves in this step and all remaining steps so as to prevent transmitting a pathogen. In some embodiments various substances may be used to initially clean and disinfect the wound including, without limitation, strong acidified electrolyzed water (SAEW method). In a non-limiting example, disinfecting solutions that may be used in this step include, without limitation, Aloe (aloe vera), Calendula (*calendula officinalis*), Marshmellow (*althaea officinalis*), Tea tree oil (*melaleuca alternifolia*), Gotu Kola (*centella asiatica*), Chamomile (*matricaria recutita* r *chamaemelum nobile*), Echinacea or coneflower (*Echinacea* spp), Slippery elm bark (*ulmus ubra* or *fulva*), Arnica, Calendula, Staphysagria, Ledum, Urtica, Hypericum, Wala, Lavender (*lavandula*), Thyme (*thymus vulgaris*), Ocimum, Oregano, Hyssop, Thieves, Clove, Elemi, Myrrh, Melrose, Honey and olive oil, Sage (*salvia*), Colloidal silver, MIROR EPF TM—(Clove oil, mint oil, rosemary oil, thyme oil, plant esters, eugenol, distilled water), Goldenseal (*hydrastis Canadensis*), Dandelion (*Taraxacum officinale*), Pycnogenol (*pinus pinaster*), Bloodroot (*Sanguinaria canadensis*), Comfrey (*symphytum officinale*), Burdock (*arctium lappa*), Bistort (*persicaria bistorta*), Fenugreek (*foeniculum vulgare*), Figwort (*scrophularia nodosa*), Carline Thistle (*carlina acaulis*)—wound irrigation, Horsetail (*equisetum arvense*), Chaparral (*larrea tridentate*), Balsam of Peru (*myroxylon balsamum*), Pineapple (*ananas comosus*, bromelainum, pineapple enzyme), Daisy (bairnwort, bruisewort), Calendula Flower (*calendula officinalis*), Horse Chestnut Seed Extract (*aesculus hippocastanum*), Rosemary Leaf (*rosmarinus offlinalis*), and Citric Acid.

In step 105, the wound may be further disinfected by applying a deep cleaning antibacterial cleansing solution with a sterile cotton swab, eyedropper, or other type of applicator to the wound and surrounding area. The type of applicator may be determined by the size or depth of the wound. For example, without limitation, a long cotton swab may be used to apply the solution to a deep wound. It is contemplated that various different antibacterial solutions may be used such as, but not limited to, Sol-U-Guard™ Botanical 2× Concentrate diluted, oil of thyme and citric acid, ammonium hydroxide, sodium lauryl sulfate, etc. In a non-limiting example, disinfecting solutions that may be used in this step include, without limitation, Aloe (aloe vera), Calendula (*calendula officinalis*), Marshmellow (*althaea officinalis*), Tea tree oil (*melaleuca alternifolia*), Gotu Kola (*centella asiatica*), Chamomile (*matricaria recutita* r *chamaemelum nobile*), Echinacea or coneflower (*Echinacea* spp), Slippery elm bark (*ulmus ubra* or *fulva*), Arnica, Calendula, Staphysagria, Ledum, Urtica, Hypericum, Wala, Lavender (*lavandula*), Thyme (*thymus vulgaris*), Ocimum, Oregano, Hyssop, Thieves, Clove, Elemi, Myrrh, Melrose, Honey and olive oil, Sage (*salvia*), Colloidal silver, MIROR EPF TM—(Clove oil, mint oil, rosemary oil, thyme oil, plant esters, eugenol, distilled water), Goldenseal (*hydrastis Canadensis*), Dandelion (*Taraxacum officinale*), Pycnogenol (*pinus pinaster*), Bloodroot (*Sanguinaria canadensis*), Comfrey (*symphytum officinale*), Burdock (*arctium lappa*), Bistort (*persicaria bistorta*), Fenugreek (*foeniculum vulgare*), Figwort (*scrophularia nodosa*), Carline Thistle (*carlina acaulis*)—wound irrigation, Horsetail (*equisetum arvense*), Chaparral (*larrea tridentate*), Balsam of Peru (*myroxylon balsamum*), Pineapple (*ananas comosus*, bromelainum, pineapple enzyme), Daisy (bairnwort, bruisewort), Calendula Flower (*calendula officinalis*), Horse Chestnut Seed Extract (*aesculus hippocastanum*), Rosemary Leaf (*rosmarinus offlinalis*), and Citric Acid.

In some embodiments the solution applied may also be antifungal, antiseptic, analgesic, antibiotic, homeostatic, and/or vulnerary. In a particular embodiment, the Sol-U-Guard™ may be diluted in sterile water purified by reverse osmosis, spring water, or another type of purified water in a one to one ratio. In another embodiment, A 2× concentrated cleansing composition may be made by heating water purified by reverse osmosis to 50° C. in a tared vessel. Citric acid may then be added to the water, and the solution may be agitated until the citric acid is dissolved. Then, ammonia may be added, followed by the addition of sodium lauryl sulfate. The solution is typically mixed well after each addition. Thyme oil may then be added, and mixing is continued until the solution is completely clear. In this embodiment the amount of each ingredient measured as a percentage by mass of the total weight of the composition (WW %) may be as follows: reverse osmosis water 87.973 WW % to 88.173 WW %, Citric acid 4.000 WW %, Ammonium Hydroxide (29.4% ammonia) FCC 0.730 WW %, Sodium Lauryl Sulfate (29% active) 6.897 WW %, White thyme oil (46% thymol) 0.200 WW % to 0.400 WW %. Those skilled in the art will readily recognize, in light of and in accordance with the teachings of the present invention, that various different combinations of ingredients may be combined using various different methods to create a multiplicity of suitable disinfecting and cleansing solutions. In a non-limiting example, disinfecting solutions that may be used in this step include, without limitation, Aloe (aloe vera), Calendula (*calendula officinalis*), Marshmellow (*althaea officinalis*), Tea tree oil (*melaleuca alternifolia*), Gotu Kola (*centella asiatica*), Chamomile (*matricaria recutita* r *chamaemelum nobile*), Echinacea or coneflower (*Echinacea* spp), Slippery elm bark (*ulmus ubra* or *fulva*), Arnica, Calendula, Staphysagria, Ledum, Urtica, Hypericum, Wala, Lavender (*lavandula*), Thyme (*thymus vulgaris*), Ocimum, Oregano, Hyssop, Thieves, Clove, Elemi, Myrrh, Melrose, Honey and olive oil, Sage (*salvia*), Colloidal silver, MIROR EPF TM—(Clove oil, mint oil, rosemary oil, thyme oil, plant esters, eugenol, distilled water), Goldenseal (*hydrastis Canadensis*), Dandelion (*Taraxacum officinale*), Pycnogenol (*pinus pinaster*), Bloodroot (*Sanguinaria canadensis*), Comfrey (*symphytum officinale*), Burdock (*arctium lappa*), Bistort (*persicaria bistorta*), Fenugreek (*foeniculum vulgare*), Figwort (*scrophularia nodosa*), Carline Thistle (*carlina acaulis*)—wound irrigation, Horsetail (*equisetum arvense*), Chaparral (*larrea tridentate*), Balsam of Peru (*myroxylon balsamum*), Pineapple (*ananas comosus*, bromelainum, pineapple enzyme), Daisy (bairnwort, bruisewort), Calendula Flower (*calendula officinalis*), Horse Chestnut Seed Extract (*aesculus hippocastanum*), Rosemary Leaf (*rosmarinus officinalis*), and Citric Acid.

Referring again to FIG. 1, in step 110, the wound may be further disinfected with a disinfectant that may penetrate into the wound and may remain on the wound for an extended amount of time. This disinfectant may be applied on and around the wound to saturate the wound with an applicator such as, but not limited to, a sterile cotton swab, an eyedropper, a finger, etc. Again, the type of applicator may be determined by the area or depth of the wound. In the present embodiment, tea tree oil (*Melaleuca Alternifolia*) is used as this deep penetrating disinfectant as it is believed to have antiviral, antibacterial, antifungal, anti-inflammatory, antiseptic, antioxidant, anti-parasitic, immune stimulating, insecticidal, tissue regenerating, and decongesting properties. However, a multiplicity of suitable substances may be used in various different embodiments such as, but not limited to, silver water, oregano oil, hyssop oil, thieves oil, clove, myrrh, melrose, elemi, etc. In a non-limiting example, disinfecting solutions that may be used in this step include, without limitation, Aloe (aloe vera), Calendula (*calendula officinalis*), Marshmellow (althaea *officinalis*), Tea tree oil (*melaleuca alternifolia*), Gotu Kola (*centella asiatica*), Chamomile (*matricaria recutita* r *chamaemelum nobile*), Echinacea or coneflower (*Echinacea* spp), Slippery elm bark (*ulmus ubra* or *fulva*), Arnica, Calendula, Staphysagria, Ledum, Urtica, Hypericum, Wala, Lavender (*lavandula*), Thyme (*thymus vulgaris*), Ocimum, Oregano, Hyssop, Thieves, Clove, Elemi, Myrrh, Melrose, Honey and olive oil, Sage (*salvia*), Colloidal silver, MIROR EPF TM— (Clove oil, mint oil, rosemary oil, thyme oil, plant esters, eugenol, distilled water), Goldenseal (*hydrastis Canadensis*), Dandelion (*Taraxacum officinale*), Pycnogenol (*pinus pinaster*), Bloodroot (*Sanguinaria canadensis*), Comfrey (*symphytum officinale*), Burdock (*arctium lappa*), Bistort (*persicaria bistorta*), Fenugreek (*foeniculum vulgare*), Figwort (*scrophularia nodosa*), Carline Thistle (*carlina acaulis*)—wound irrigation, Horsetail (*equisetum arvense*), Chaparral (*larrea tridentate*), Balsam of Peru (*myroxylon balsamum*), Pineapple (*ananas comosus*, bromelainum, pineapple enzyme), Daisy (bairnwort, bruisewort), Calendula Flower (*calendula officinalis*), Horse Chestnut Seed Extract (*aesculus hippocastanum*), Rosemary Leaf (*rosmarinus officinalis*), and Citric Acid.

In step 115, a disinfectant may be applied to the perimeter of the wound with a sterile cotton swab or other type of applicator, taking care not to place the disinfectant directly on or in the wound. In the present embodiment, Betadine, a commercial antibacterial solution, is used as the disinfectant; however, various disinfectants may be applied to the perimeter of the wound in alternate embodiments such as, but not limited to, mercurochrome, thymol, merthiolate, mupirocin, Aloe (aloe vera), Calendula (*calendula officinalis*), Marshmellow (althaea *officinalis*), Tea tree oil (*melaleuca alternifolia*), Gotu Kola (*centella asiatica*), Chamomile (*matricaria recutita* r *chamaemelum nobile*), Echinacea or coneflower (*Echinacea* spp), Slippery elm bark (*ulmus ubra* or *fulva*), Arnica, Calendula, Staphysagria, Ledum, Urtica, Hypericum, Wala, Lavender (*lavandula*), Thyme (*thymus vulgaris*), Ocimum, Oregano, Hyssop, Thieves, Clove, Elemi, Myrrh, Melrose, Honey and olive oil, Sage (*salvia*), Colloidal silver, MIROR EPF TM— (Clove oil, mint oil, rosemary oil, thyme oil, plant esters, eugenol, distilled water), Goldenseal (*hydrastis Canadensis*), Dandelion (*Taraxacum officinale*), Pycnogenol (*pinus pinaster*), Bloodroot (*Sanguinaria canadensis*), Comfrey (*symphytum officinale*), Burdock (*arctium lappa*), Bistort (*persicaria bistorta*), Fenugreek (*foeniculum vulgare*), Figwort (*scrophularia nodosa*), Carline Thistle (*carlina acaulis*)—wound irrigation, Horsetail (*equisetum arvense*), Chaparral (*larrea tridentate*), Balsam of Peru (*myroxylon balsamum*), Pineapple (*ananas comosus*, bromelainum, pineapple enzyme), Daisy (bairnwort, bruisewort), Calendula Flower (*calendula officinalis*), Horse Chestnut Seed Extract (*aesculus hippocastanum*), Rosemary Leaf (*rosmarinus officinalis*), and Citric Acid.

In many embodiments, the acidified water is a first step to cleanse and disinfect a wound. It is important to control or eradicate the infection in order for the wound to heal properly. The next step is to apply the Sol-u-guard™ which adds another layer of disinfection and handles other potential pathogens in and around the wound. Finally, Tea tree oil will help disinfect the wound but as an oil it creates a layer or seal on the wound to promote healing. In addition, nutritional supplements aid in promoting healing.

In step 120, a cold laser treatment is applied on and around the wound. The laser may typically be placed approximately 1 cm away from the wound if it is an open wound. If the wound is covered, the laser may be placed directly on the wound dressing. It is believed the cold laser may increase circulation, control pain, and aid in tissue regeneration. If the wound is in a weight bearing location such as, but not limited to, on the foot or the ankle, the cold laser may also be applied to surrounding non-ulcerated or non-wounded tissue to potentially increase the blood circulation, decrease inflammation and strengthen the bone. In the present embodiment, the cold laser may be, but not limited to, a class one laser manufactured by Multi Radiance Medical or other MFR comprising 660 nanometer (nm) wavelength red light, 875 nm infrared red light, 905 nm superpulsed light, and a static magnetic field of 35 transverse magnetic (TM). In typical use of the laser, these components may be applied simultaneously in five minute treatments using a 5 Hertz cycle. It is believed that the shorter light wavelength, lower power, different pulsing frequency, and longer treatment duration may combine to enable this cold laser method to perform better than existing commonly used laser treatment methods. For example, without limitation, typically, this cold laser method does not create inflammation or damage to the tissue. It is contemplated that the lasers in some alternate embodiments may comprise various different components such as, but not limited to, different types of light or magnetic field, heat, vibration, etc.

At the onset of treatment, the wound is tested for infectious pathogens including, without limitation, Methicillin-resistant *Staphylococcus aureus* (MRSA). In step 125 these results are reviewed to determine if an infectious pathogen is present. If so, an antibiotic substance may be applied to the wound with a cotton swab or a rubber glove in step 130. To eliminate MRSA an antibiotic solution specific for MRSA must typically be used such as, but not limited to, Vancomycin/Mupirocin 5-1.9% Ointment. In some applications antibiotics to eliminate various different infectious pathogens may be applied during this step. The caregiver should typically wear a protective glove to help prevent the spread of the pathogen. Due to the increased likelihood of a diabetic patient contracting an infectious pathogen, antibiotic treatments may be applied to the wounds of diabetic patients or other patients that may be susceptible to infection such as, but not limited to, patients on immune suppressing drugs or in the elderly, even when an infectious pathogen is not obviously present. If no infectious pathogen is present or likely to be contracted, step 130 may be skipped. In step 135 a dry, sterile gauze bandage and wrap may be applied on and around the wound to cover and protect the wound as needed and to help promote healing. In some cases, for example, without limitation, if the wound is small or nearly healed, this step may be omitted.

In other embodiments, alternative equivalent agents may be used in accordance with the teachings herein. These alternative equivalent agents may be employed in a form, strength, and frequency of application that is consistent with a therapeutic application thereof.

Figure 2:
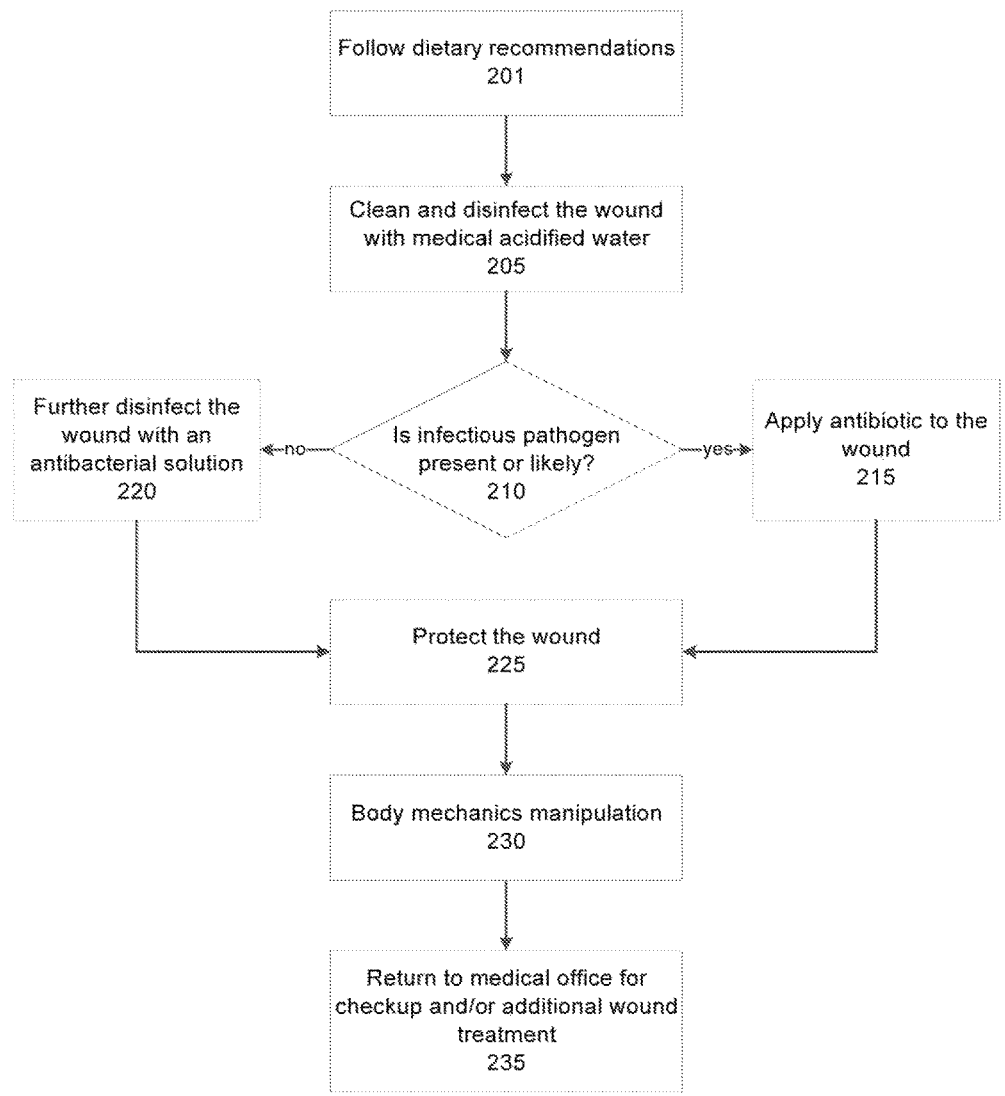
FIG. 2 is a flowchart illustrating an exemplary process for at home wound treatment, in accordance with an embodiment of the present invention.

FIG. 2 is a flowchart illustrating an exemplary process for at home wound treatment, in accordance with an embodiment of the present invention. In the present embodiment, after an in office treatment as illustrated by way of example in FIG. 1 is applied to a wound, the patient may be given detailed home care instructions designed to educate the patient, caregiver, general public, etc. to the wound healing process and localized wound care. These instructions may include without limitation a nutritional protocol with the use of multiple nutraceuticals, vitamins, and supplements which may be followed by the patient in step 201. Typically, the patient is conscious and uses normal oral means to ingest the nutrients. An example of such a protocol may be as follows: Vitamin A Caps in the dosage of 25000 IU to be taken daily at night, Vitamin D3 in the dosage of 5000 IU to be taken daily in the morning with food, COQ10 with mitochondrial support (Pyrroloquinoline Quinone or PPQ) in the dosage of 600 mg to be taken in the morning, Chelated Zinc in the dosage of 25 mg taken twice a day, Fish Oil in the dosage of 1200 mg to be taken twice a day, purified oxyhexanoic acid or other omega 3 analog in the dosage of 500 mg to 1000 mg per day, 500 mg of Vitamin C daily. 400 IU of Vitamin E daily, probiotics daily, etc. Those skilled in the art will readily recognize, in light of and in accordance with the teachings of the present invention that a multiplicity of suitable nutritional guidelines may be given to patients in alternate embodiments. For example, without limitation, substitutions or elimination of some items may occur if the patient has allergies to the items. It is believed that proper nutrition and the intake of some particular nutrients may help boost the immune system and the ability of the body to heal itself. In step 205 of the present embodiment, the patient or a caregiver may apply medical acidified water on and around the wound. Those skilled in the art will readily recognize, in light of and in accordance with the teachings of the present invention, that a multiplicity of suitable substances may be used to clean and disinfect the wound in this step including, without limitation, mercurochrome, thymol, merthiolate, mupirocin, Aloe (*aloe vera*), Calendula (*calendula officinalis*), Marshmellow (*althaea officinalis*), Tea tree oil (*melaleuca alternifolia*), Gotu Kola (*centella asiatica*), Chamomile (*matricaria recutita* r *chamaemelum nobile*), Echinacea or coneflower (*Echinacea* spp), Slippery elm bark (*ulmus ubra* or *fulva*), Arnica, Calendula, Staphysagria, Ledum, Urtica, Hypericum, Wala, Lavender (*lavandula*), Thyme (*thymus vulgaris*), Ocimum, Oregano, Hyssop, Thieves, Clove, Elemi, Myrrh, Melrose, Honey and olive oil, Sage (*salvia*), Colloidal silver, MIROR EPF TM— (Clove oil, mint oil, rosemary oil, thyme oil, plant esters, eugenol, distilled water), Goldenseal (*hydrastis Canadensis*), Dandelion (*Taraxacum officinale*), Pycnogenol (*pinus pinaster*), Bloodroot (*Sanguinaria canadensis*), Comfrey (*symphytum officinale*), Burdock (*arctium lappa*), Bistort (*persicaria bistorta*), Fenugreek (*foeniculum vulgare*), Figwort (*scrophularia nodosa*), Carline Thistle (*carlina acaulis*)—wound irrigation, Horsetail (*equisetum arvense*), Chaparral (*larrea tridentate*), Balsam of Peru (*myroxylon balsamum*), Pineapple (*ananas comosus*, bromelainum, pineapple enzyme), Daisy (bairnwort, bruisewort), Calendula Flower (*calendula officinalis*), Horse Chestnut Seed Extract (*aesculus hippocastanum*), Rosemary Leaf (*rosmarinus officinalis*), and Citric Acid.

The patient or caregiver should always wear protective gloves. In step 210 if an infectious pathogen is present or the wound is septic, an antibiotic may be applied to the wound with a sterile rubber glove or cotton swab in step 215. For example, without limitation Vancomycin/Mupirocin 5-1.9% Ointment may be used to treat MRSA. This step may be particularly beneficial for patients with diabetes because of the typically increased likelihood of infections in diabetic patients. If an infectious pathogen is not present or likely in step 210, the patient or caregiver may instead disinfect the wound in step 220 with an antibacterial solution such as, but not limited to, Sol-U-Guard™ Botanical 2× Concentrate or citric acid and thyme oil as an ointment. Again, it is contemplated that a multiplicity of suitable substances may be used to disinfect the wound in this step. In step 225 the wound by be protected by the application of a sterile gauze bandage and wrap on and around the wound. In some cases, the wound may not require protection, and this step may be omitted. If necessary, the patient may then return to the medical office for a checkup or for additional treatment to the wound in step 235. In some alternate embodiments, this at home wound treatment process may be performed alone rather than in conjunction with an in office wound treatment process as described by way of example in accordance with FIG. 1. In some embodiments, the use of Vancomycin/Mupirocin may be omitted.

In some embodiments, body mechanics manipulation may be performed by chiropractic or osteopathic practitioner, a physical therapist, a massage therapist, or another qualified individual to correct abnormal structural biomechanics of appropriate areas that may facilitate better use of the body in step 230. For example, without limitation, lower extremities may be adjusted to help prevent disuse atrophy, alteration of gait or movement, or pain from compensation due to the wound. Manipulative techniques to adjust body mechanics may improve function of the afflicted portions of the body which may assist with wound healing. In a non-limiting example, improving a person's biomechanics may allow that person to become more ambulatory. Individuals who are bed ridden or immobile may develop generalized disuse atrophy. Bed or pressure sores are also a complication of being bed ridden. It is believed that improvements of circulatory conditions, bone strength, and muscle conditioning are enhanced through optimal biomechanical performance and better enable the individual to become ambulatory. In some embodiments, this procedure is optional but may considerably improve the overall function of the individuals who implements this as a part of his or her treatment program. In some embodiments, this is an in office procedure that should be administered after the wound treatment.

In typical use of an embodiment of the present invention, an acute or chronic wound may be treated by processes that may eliminate dirt, unwanted bacteria and other pathogens from the wound with the use of sterilizers and sanitizers. Our method addresses the wound care amelioration which yields swift cost effective results. Some embodiments may be less expensive than currently used procedures since many of the ingredients used may be affordable to average income households. Moreover, the healing time for an acute or chronic wound currently may be upwards of fifteen weeks or more, while some embodiments of the present invention may possibly heal an acute or chronic wound in eight weeks or less.

Figure 3:
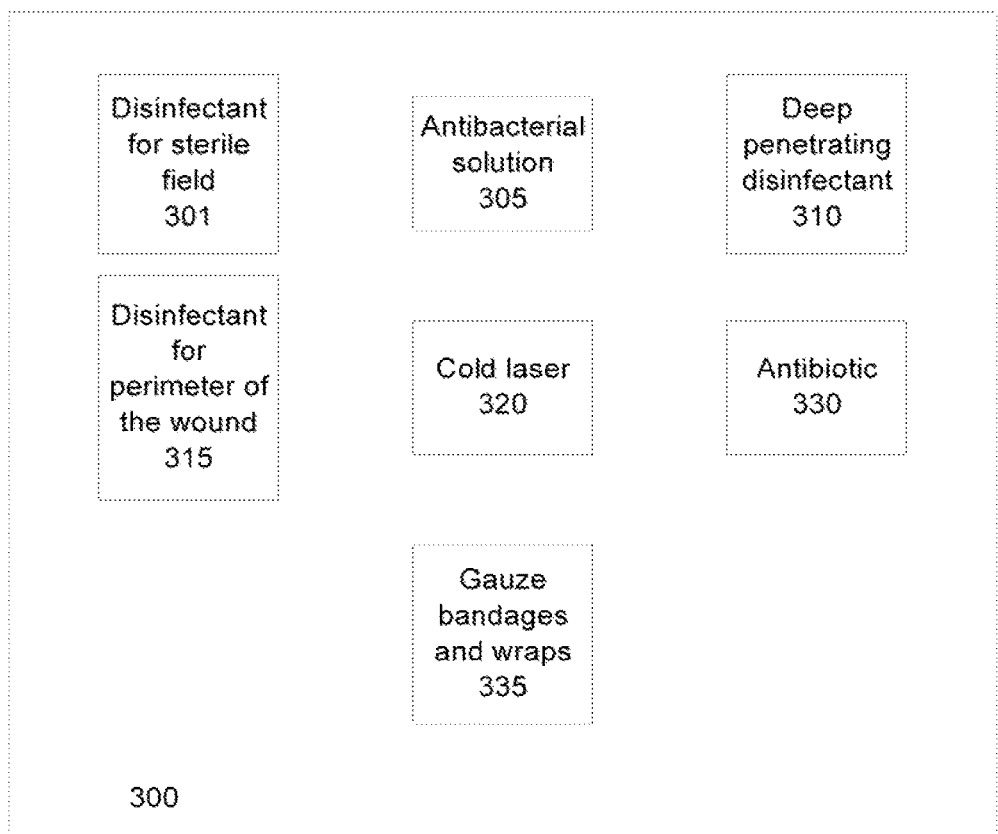
FIG. 3 illustrates an exemplary system for in office treatment, in accordance with an embodiment of the present invention.

FIG. 3 illustrates an exemplary system for in office treatment, in accordance with an embodiment of the present invention. System 300 includes, without limitation, basic elements for wound treatment in a doctor's office, hospital, clinic, etc. in accordance with the teaching of the present invention. Disinfectant 301 may include, without limitation, a supply of disinfectant for the initial application to the wound to provide a sterile field. In some embodiments, disinfectant 301 may include, without limitation, medical acidified water with a pH balance about between 2.54 and 5.72. In some alternate embodiments, disinfectant 301 may include an apparatus to produce medical acidified water in the office such as, but not limited to, a Biontech BTM3000 machine to convert spring water or water purified by reverse osmosis into acidified water in a 60 minute cycle. In other embodiments, other disinfecting solutions may be included such as, but not limited to, those described in conjunction with step 101. Antibacterial solution 305 may include, without limitation, a supply of a deep cleaning antibacterial cleansing solution. In some embodiments various different antibacterial solutions may be included such as, but not limited to, Sol-U-Guard™ Botanical 2× Concentrate diluted, oil of thyme and citric acid, ammonium hydroxide, sodium lauryl sulfate, and those described in conjunction with step 105. Deep penetrating disinfectant 310 may include, without limitation, a supply of tea tree oil (*Melaleuca Alternifolia*) as it is believed to have antiviral, antibacterial, antifungal, anti-inflammatory, antiseptic, antioxidant, anti-parasitic, immune stimulating, insecticidal, tissue regenerating, and decongesting properties. In other embodiments, deep penetrating disinfectant 310 may include solutions such as, but not limited to, those described in conjunction with step 110. Disinfectant 315 may include, without limitation, a supply of Betadine to be applied to the perimeter of the wound. In other embodiments, various other disinfectants may be included such as, but not limited to, those described in conjunction with step 115. Cold laser 320 may include, but not limited to, a class one laser manufactured by Multi Radiance Medical or other MFR comprising 660 nanometer (nm) wavelength red light, 875 nm infrared red light, 905 nm super-pulsed light, and a static magnetic field of 35 transverse magnetic (TM). Antibiotic 330 may include a supply of, without limitation, Vancomycin/Mupirocin 5-1.9% Ointment for infectious pathogens including Methicillin-resistant *Staphylococcus aureus* (MRSA). In other embodiments, antibiotic 330 may include other antibiotics. In some embodiments, system 300 may include a supply of sterile gauze bandages and wraps 335 that may be applied on and around the wound. In some embodiments, system 300 may also include, without limitation, instructions for the in office wound treatment, in accordance with the teachings herein. In some alternate embodiments, system may also include, without limitation, instructions for the patient or caregiver for in home treatment, in accordance with the teachings herein. In some alternate embodiments, system 300 may also include, without limitation, multiple nutraceuticals, vitamins, and supplements which may be provided to the patient. In some alternate embodiments, portions of system 300 may be provided to the doctor's office, hospital, clinic, etc. such as, but not limited to, replacement for exhausted supplies or inoperative equipment.

Those skilled in the art will readily recognize, in light of and in accordance with the teachings of the present invention, that some approaches may only employ an in office treatment or an at home treatment. For example, without limitation, some embodiments may be configured as systems that may be used by individuals to treat wounds in non-medical environments such as, but not limited to, wound healing kits, survival kits, first aid kits, military medical aid kits Such embodiments may be used by a wide range of individuals in various different situations including, without limitation, diabetics, post-surgical patients, parents of pediatric patients, EMTs or other emergency personnel at accident scenes, military personnel in field hospital or battleground situations, pet owners, home care givers, school nurses, $3^{rd}$ world treatment situations, etc. In addition, it is contemplated that some embodiments may be implemented that may be used by pet owners to treat wounds on various different types of animals including, but not limited to dog, cats, horses, etc. Furthermore, in some embodiments medical or surgical wound care packs may be configured specifically for used in medical environments such as, but not limited to, emergency rooms, doctors' offices, operating rooms, hospital recovery or intensive care units, veterinary hospitals, wound care centers, etc. Additionally, various different types of wounds may be treated by some embodiments such as, but not limited to, diabetic foot ulcers (DFU's), neurotrophics ulcers, chronic wounds, post-surgical wounds, first aid care, burns, scrapes, bruises.

Those skilled in the art will readily recognize, in light of and in accordance with the teachings of the present invention, that any of the foregoing steps may be suitably replaced, reordered, or removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. For any method steps described in the present application that can be carried out on a computing machine, a typical computer system can, when appropriately configured or designed, serve as a computer system in which those aspects of the invention may be embodied.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" claim limitation implies that the broadest initial search on 112(6) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112 (6) when such corresponding structures are not explicitly disclosed in the foregoing patent specification. Therefore, for any invention element(s)/structure(s) corresponding to functional claim limitation(s), in the below claims interpreted under 35 USC § 112 (6), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112 (6) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112 (6), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing a method and apparatus treat acute and chronic wounds according to the present invention will be apparent to those skilled in the art. Various aspects of the invention have been described above by way of illustration, and the specific embodiments disclosed are not intended to limit the invention to the particular forms disclosed. The particular implementation of the method and apparatus to treat acute and chronic wounds may vary depending upon the particular context or application. By way of example, and not limitation, the wound treating methods described in the foregoing were principally directed to implementations for treating external wounds; however, similar techniques may instead be applied to applications for healing internal wounds with a cold laser, nutritional strategies and body mechanics manipulation, which implementations of the present invention are contemplated as within the scope of the present invention. For example, without limitation, a cold laser may be applied to broken bones, sprains, internal bleeding, surgical sites, etc. to potentially speed healing. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims. The following claims are hereby incorporated into the detailed description, with each claim standing on its own as a separate embodiment.

What is claimed is:

1. A method comprising the steps of:
    applying in a first step of treating a wound in a medical setting, a first disinfecting solution on and around a wound, in which said first disinfecting solution comprises at least a medical acidified water;
    applying said first disinfecting solution with a first applicator device, in which said first applicator device comprises at least a sprayer;
    applying, in a second step of treating the wound in said medical setting, a second disinfecting solution on and around the wound, in which said second disinfecting solution comprises a combination of water, citric acid, ammonium hydroxide, sodium lauryl sulfate, and thyme oil, all mixed together;
    applying said mixture of water, citric acid, ammonium hydroxide, sodium lauryl sulfate, and thyme oil solution with a second applicator device, in which said second applicator device comprises at least a sterile cotton swab;
    applying, in a third step of treating the wound in said medical setting, an amount of a third disinfecting solution on and around the wound, in which said third disinfecting solution comprises at least a tea tree oil;

applying said tea tree oil with a third applicator device, in which third applicator device comprises at least an eyedropper;

applying, in a fourth step of treating the wound in said medical setting, an amount of a fourth disinfecting solution around the wound, in which said fourth disinfecting solution comprises a betadine;

applying said betadine with a fourth applicator device, in which said fourth applicator device comprises at least one of, a sterile cotton swab and an eyedropper;

applying, in a fifth step of treating the wound in said medical setting, a treatment of a proximate red light cold laser of approximately 660 nanometer (nm) wavelength on and around the wound;

applying said approximately 660 nanometer (nm) wavelength red light cold laser treatment performed in a plurality of treatments sessions, wherein said cold laser is applied with a certain pulsing frequency duty cycle;

testing the wound for infectious pathogens including Methicillin-resistant Staphylococcus aureus (MRSA);

applying, based on said testing step, a Vancomycin or Mupirocin Ointment to the wound with a cotton swab or a rubber glove if said infectious pathogens are present; and, applying a sterile gauze bandage and wrap for covering the wound.

2. The method as recited in claim 1, further comprising the steps of following, in a first step for at home wound treatment, a nutritional protocol regarding dietary recommendations with the use of vitamins for at home wound treatment.

3. The method as recited in claim 2, further comprising the steps of disinfecting, in a second step for at home wound treatment, the wound with medical acidified water.

4. The method as recited in claim 3, further comprising the steps of applying, in a third step for at home wound treatment, Vancomycin/Mupirocin Ointment if infectious pathogens are present.

5. The method as recited in claim 4, further comprising the steps of disinfecting, in a fourth step for at home wound treatment, the wound with citric acid and thyme oil as an ointment.

6. The method as recited in claim 1, in which said cold laser emissions further comprises at least one of, an approximately 875 nanometer infrared red light, an approximately 905 nanometer super-pulsed light, and a static magnetic field of approximately 35 transverse magnetic field.

7. The method as recited in claim 1, further comprising the steps of:

receiving, in a first step for at home wound treatment, a medical acidified water on and around the wound after removal of said sterile gauze bandage and wrap;

receiving, in a second step for at home wound treatment, a composition of citric acid and thyme oil on and around the wound; and receiving, in a third step for at home wound treatment, a new sterile gauze bandage and wrap for covering the wound.

8. The method as recited in claim 7, further comprising the step of receiving manipulative techniques that is configured to adjust body mechanics.

9. The method as recited in claim 7, in which said nutritional protocol comprises at least one of, vitamin A, vitamin D3, COQ10, chelated zinc, fish oil, omega 3 analog, vitamin C, vitamin E, and probiotics.

10. The method as recited in claim 1, wherein the duration of each of said treatment sessions is approximately 5 minutes and said pulsing frequency duty cycle is approximately 5 Hertz.

11. A method comprising the steps of:

applying, in a first step of treating a wound, a first disinfecting solution on and around a wound, in which said first disinfecting solution comprises at least a citric acid;

applying said citric acid with a first applicator device, said first applicator device comprises at least an eyedropper;

applying, in a second step of treating the wound, a second disinfecting solution on and around the wound, in which said second disinfecting solution comprises a Sol-U-Guard Botanical;

applying said Sol-U-Guard Botanical with a second applicator device, said second applicator device comprises at least a sterile cotton swab;

applying, in a third step of treating the wound, a third disinfecting solution on and around the diabetic wound, in which said third disinfecting solution comprises at least one of, an oregano oil, a hyssop oil, and a thieves oil;

applying said third disinfecting solution with a third applicator device, said third applicator device comprises at least a sprayer;

applying, in a fourth step of treating the wound, a fourth disinfecting solution around the wound, in which said fourth disinfecting solution comprises at least one of, a mercurochrome, a thymol, and a merthiolate;

applying said fourth disinfecting solution with a fourth applicator device, said fourth applicator device comprises at least one of, a sterile cotton swab and eyedropper;

applying, in a fifth step of treating the wound, a proximate 905 nm super-pulsed light cold laser treatment on and around the wound;

applying said proximate 905 nm super-pulsed light cold laser treatment in five (5) minute treatments using a five (5) Hertz cycle;

testing the wound for infectious pathogens including Methicillin-resistant Staphylococcus aureus (MRSA);

reviewing a result of said testing step to determine if said infectious pathogens are present;

applying, based on said reviewing step that infectious pathogens are present, an amount of an antibiotic substance on and around the wound;

applying a sterile gauze bandage and wrap for covering the wound; and providing a home care instruction, said home care instruction comprises a nutritional protocol that is configured to aid in the wound healing process and localized wound care.

12. The method as recited in claim 11, further comprising the steps of following, in a first step of at home wound treatment, dietary recommendations with the use of vitamins in which said first disinfecting solution comprises medical acidified water.

13. The method as recited in claim 12, further comprising the steps of disinfecting, in a second step of at home wound treatment, the wound with at least one of, a calendula and a gotu kolain.

14. The method as recited in claim 13, further comprising the steps of applying, in a third step of at home wound treatment, Vancomycin/Mupirocin Ointment if infectious pathogens are present.

15. The method as recited in claim 14, further comprising the steps of disinfecting, in a fourth step of at home wound treatment, the wound with Sol-U-Guard™ Botanical as an ointment.

16. The method as recited in claim 11, in which said antibiotic substance comprises at least a vancomycin/mupirocin ointment.

17. The method as recited in claim 11, in which said cold laser treatment further comprises a static magnetic field of substantially 35 transverse magnetic wave.

18. The method as recited in claim 11, further comprising the steps of:
   receiving an acidified water solution on and around the diabetic wound after removal of said sterile gauze bandage and wrap;
   receiving an amount of said antibiotic substance on and around the wound; and
   receiving a new sterile gauze bandage and wrap covering the wound.

19. The method as recited in claim 18, further comprising the step of receiving a nutritional protocol with the use of at least one of, multiple nutraceuticals, vitamins, and supplements.

20. The method as recited in claim 19, in which said nutritional protocol comprises at least one of, a vitamin A, a vitamin D3, a COQ10, a chelated zinc, a fish oil, an omega 3 analog, a vitamin C, a vitamin E, and probiotics.

21. The method as recited in claim 18, further comprising the step of receiving manipulative techniques that are configured to adjust body mechanics.

\* \* \* \* \*